United States Patent [19]
Champaneri et al.

[11] Patent Number: 5,495,330
[45] Date of Patent: Feb. 27, 1996

[54] CONTAINER INSPECTION MACHINE HAVING SEQUENTIALLY ACCESSED COMPUTER ALIGNMENT GAGES

[75] Inventors: Jayesh K. Champaneri; Leo B. Baldwin, both of Horseheads; Robert A. Hansen, Elmira, all of N.Y.

[73] Assignee: Emhart Glass Machinery Investments Inc., Wilmington, Del.

[21] Appl. No.: 308,032

[22] Filed: Sep. 16, 1994

[51] Int. Cl.⁶ .......................... G01N 21/00; G01N 21/90; G01N 9/04; H04N 7/18
[52] U.S. Cl. .................... 356/240; 356/428; 250/223 B; 348/127; 348/130
[58] Field of Search .................................. 340/674, 676, 340/686; 348/127, 130–132; 356/240, 428; 250/223 B

[56] References Cited

U.S. PATENT DOCUMENTS

| | | | |
|---|---|---|---|
| 4,025,201 | 5/1977 | Deane | 356/240 |
| 4,280,624 | 7/1981 | Ford | 356/240 |
| 4,403,858 | 9/1983 | Yoshida | 250/223 B |
| 4,509,081 | 4/1985 | Peyton et al. | 348/127 |
| 5,256,871 | 10/1993 | Baldwin | 356/240 |

*Primary Examiner*—Frank Gonzalez
*Assistant Examiner*—Jason D. Eisenberg
*Attorney, Agent, or Firm*—Spencer T. Smith

[57] ABSTRACT

A machine for inspecting containers is disclosed which has a number of adjustable structures such as the focus, orientation and zoom of a camera and mirrors which are used to direct an image to the sensor of the camera. The computer defines a gage for each adjustment and sequentially activates the gages on the computer screen.

8 Claims, 8 Drawing Sheets

CONTAINER INSPECTION MACHINE HAVING SEQUENTIALLY ACCESSED COMPUTER ALIGNMENT GAGES

FIELD OF INVENTION

The present invention relates to machines for inspecting glass or plastic containers such as bottles.

DESCRIPTION OF RELATED ART

In state of the art machines, shown in U.S. Pat. Nos. numbered 5,256,871 and 4,025,201, two views of a container being inspected are manipulated via optical systems including periscopes, lenses, reflecting prisms and mirrors. Such systems require adjustments and this is a most difficult and confusing task.

It is accordingly an object of the present invention to make adjustments easier in such systems.

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE DRAWINGS

Referring to the drawings.

1. Camera mirror azimuth—left top;
2. Camera mirror elevation—left center;
3. Camera rotation—left bottom;
4. Right back mirror elevation—top center;
5. Left back mirror azimuth—center;
6. Left back mirror elevation—bottom center;
7. Left periscope lower mirror—top right;
8. Right periscope lower mirror—right center;
9. Right back mirror azimuth—bottom right.

Figure 4:
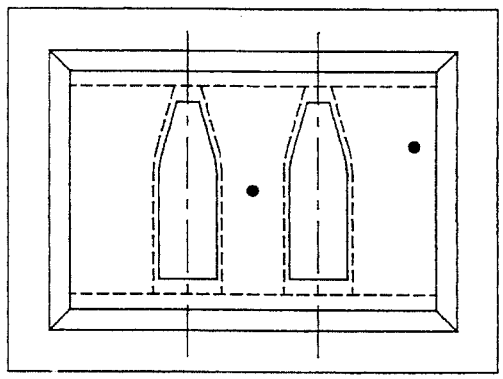
Figure 5:
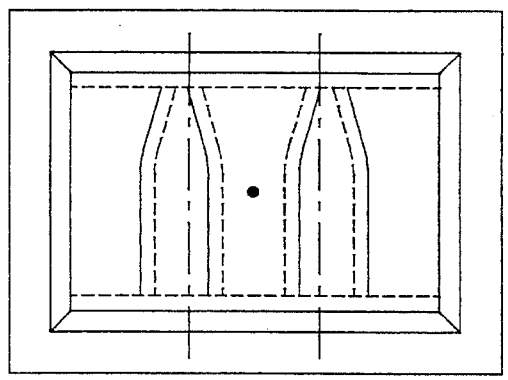
Figure 6:
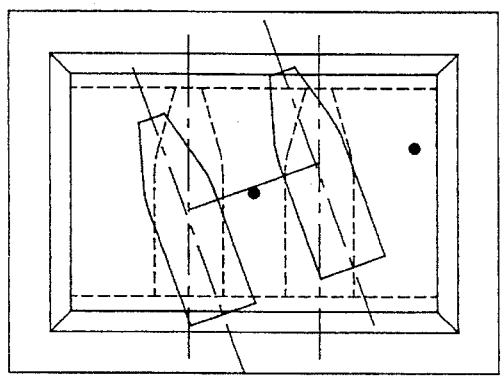
Figure 7:
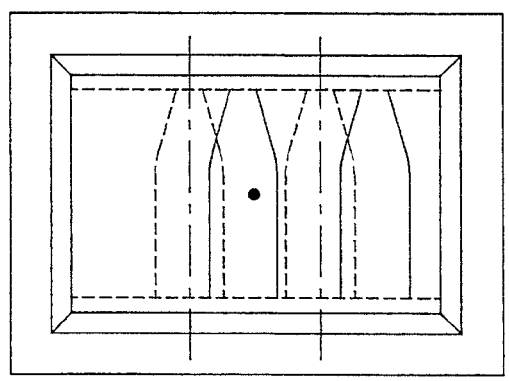
Figure 8:
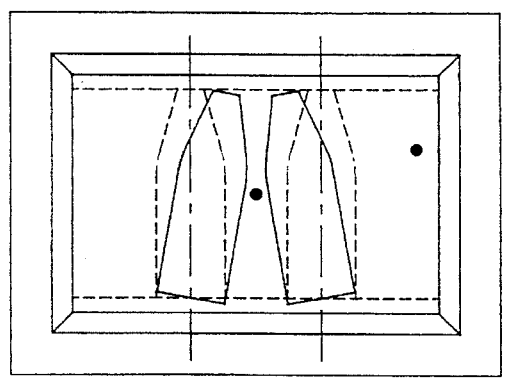
Figure 9:
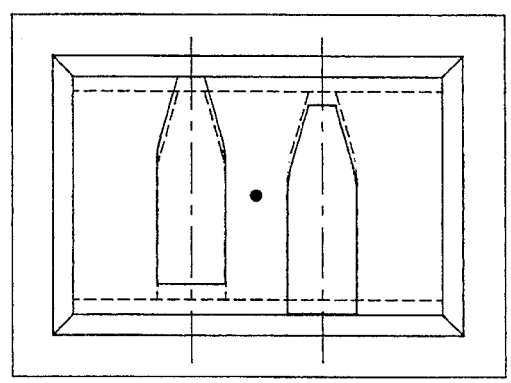

FIG. 4, illustrates the computer camera image screen which would be visible during normal operation, when the camera zoom is out of position (alignment);

FIG. 5, a view similar to FIG. 4, illustrates the computer camera image screen when the prism has been displaced to the wrong position (out of alignment);

FIG. 6, a view similar to FIG. 4, illustrates the computer camera image screen when the orientation of the camera is out of alignment;

FIG. 7, a view similar to FIG. 4, illustrates the computer camera image screen when the camera mirror is out of azimuth alignment;

FIG. 8, a view similar to FIG. 4, illustrates the computer camera image screen, illustrating the two bottle images that could be present when the left and right lower periscope mirror alignment is incorrect;

FIG. 9, a view similar to FIG. 4, illustrates the computer camera image screen when the left back and right back mirrors are out of elevational alignment.

Figure 10:
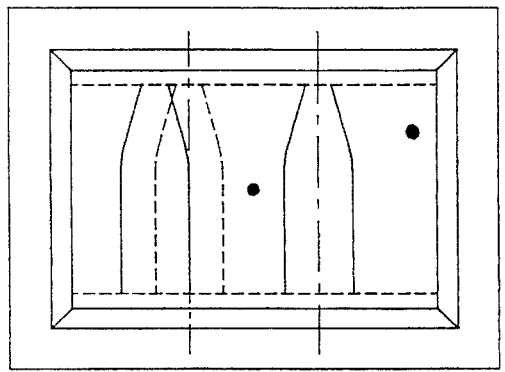
Figure 11:
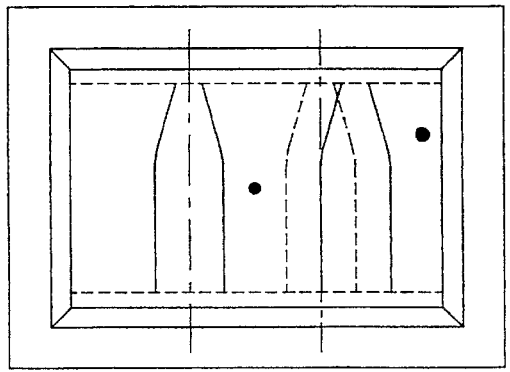
Figure 12:
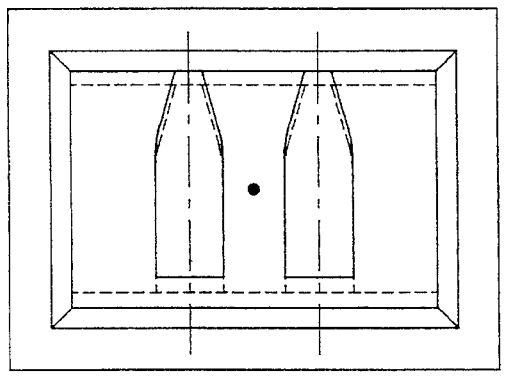
Figure 13:
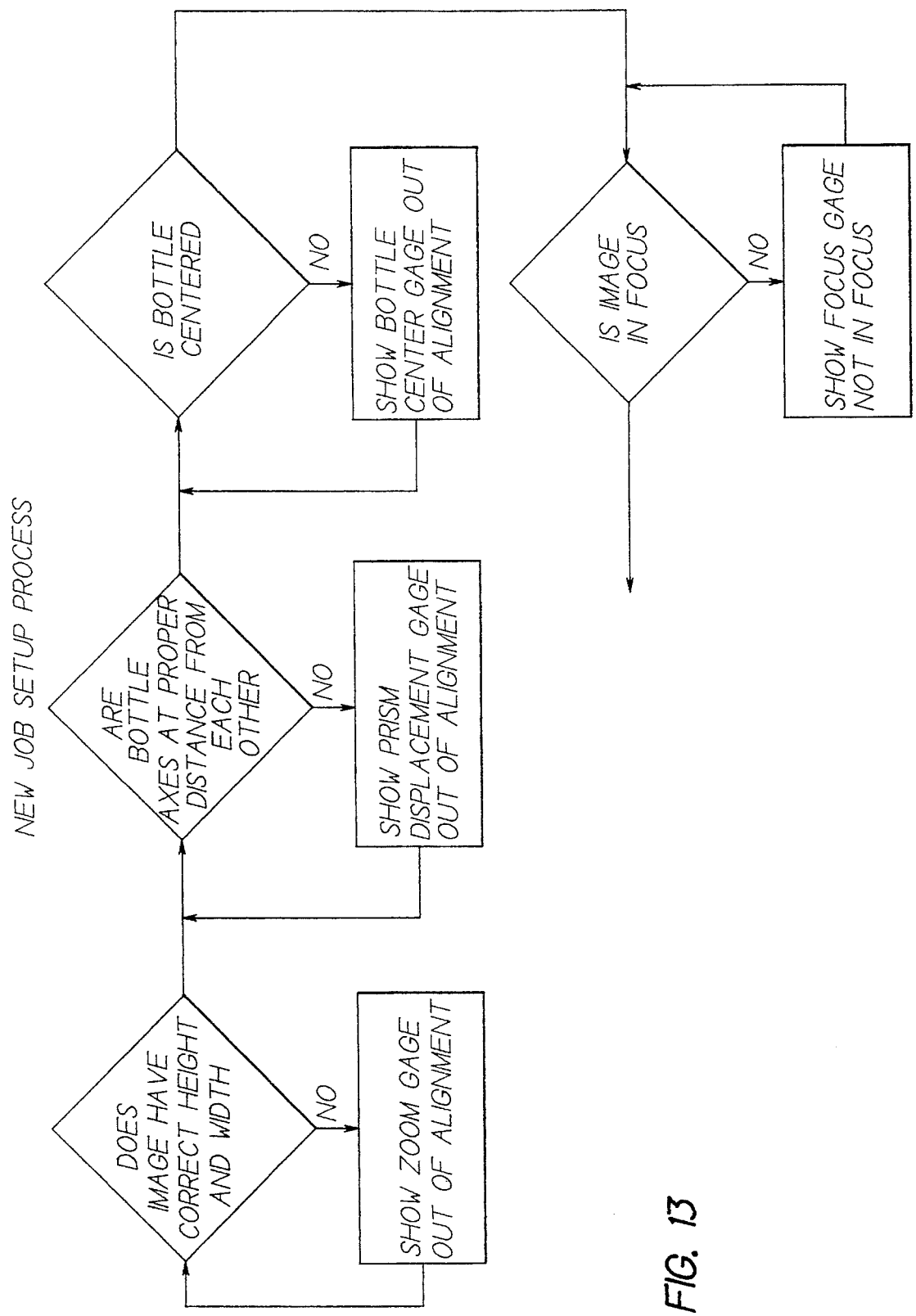

FIG. 10, a view similar to FIG. 4, illustrates the computer camera image screen when the left back mirror is out of azimuth alignment;

FIG. 11, a view similar to FIG. 4, illustrates the computer camera image screen when the right back mirror is out of azimuth alignment;

FIG. 12, a view similar to FIG. 4, illustrates the computer camera image screen when the camera mirror is out of elevational alignment;

FIG. 13 illustrates the computer flow chart for the new job setup process; and

Figure 14A:
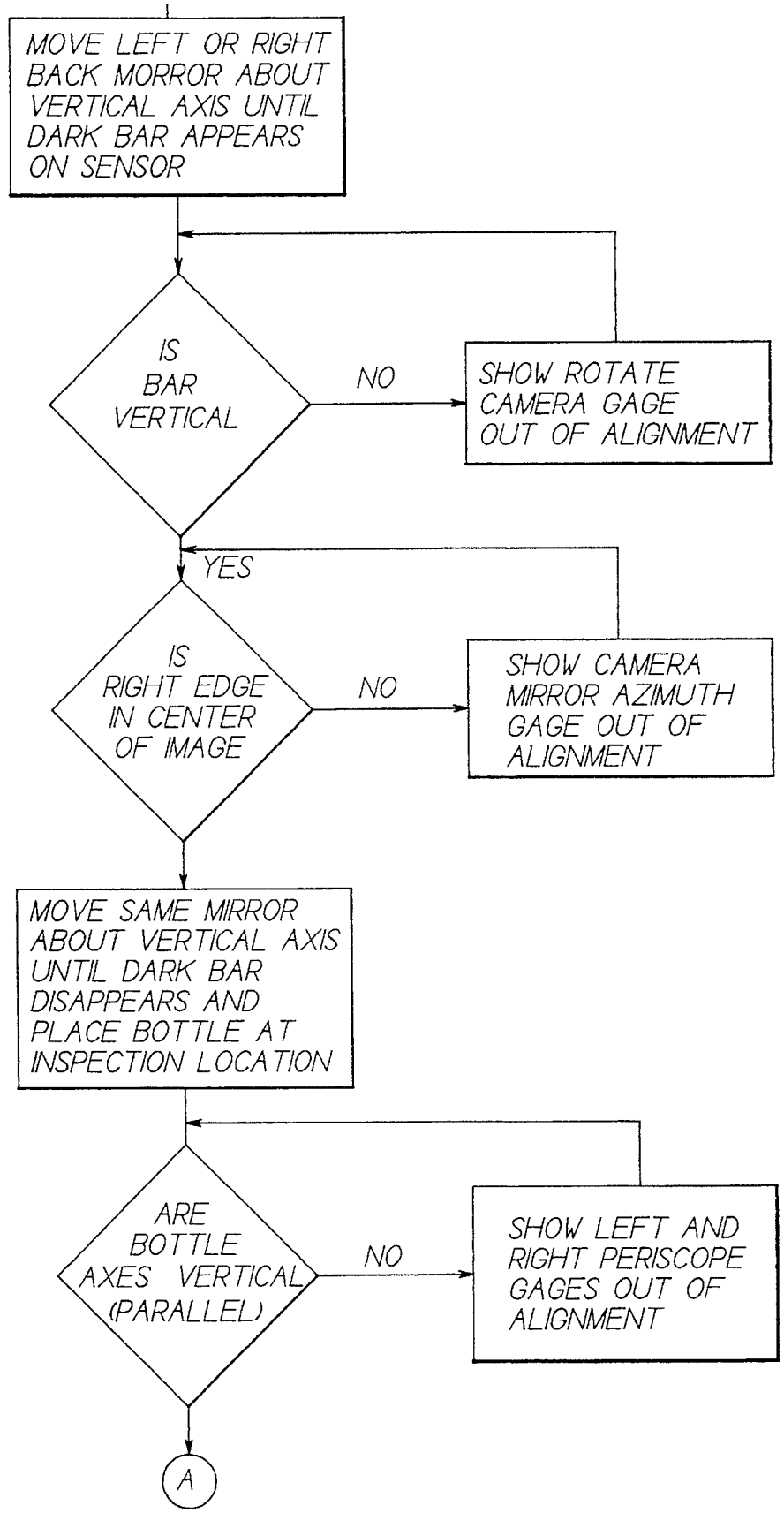
Figure 14B:
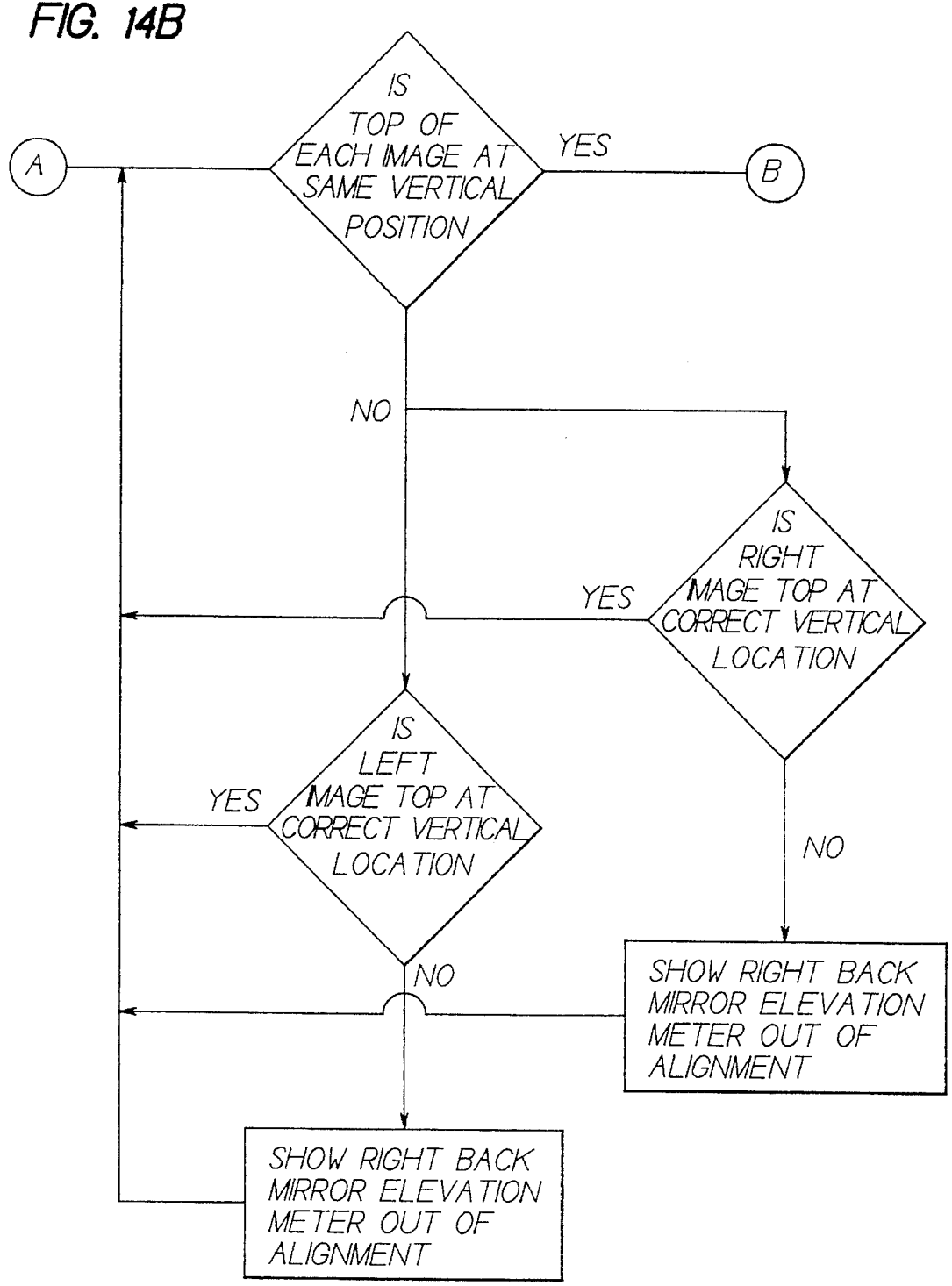
Figure 14C:
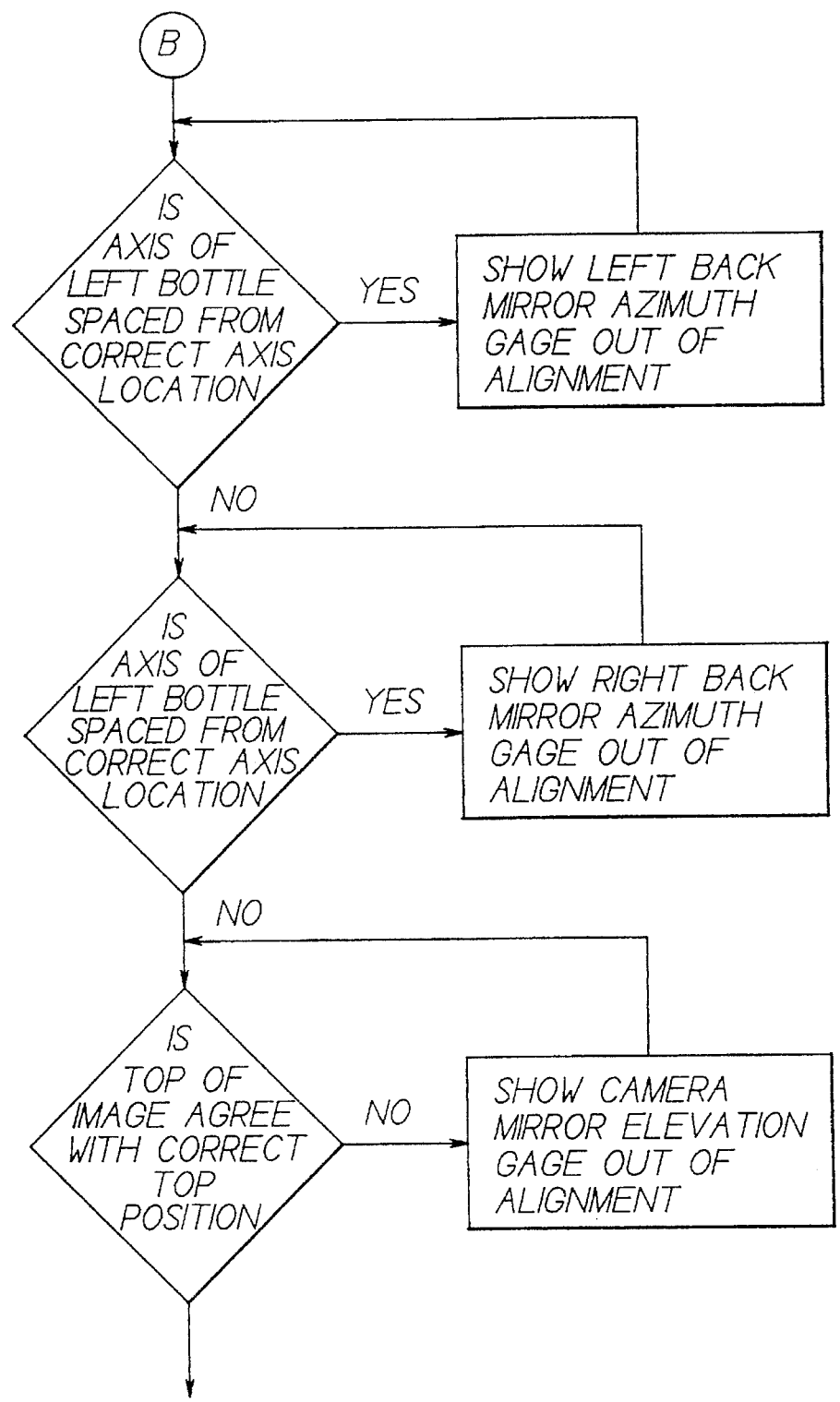

FIGS. 14A through 14C illustrate the computer flow chart for machine setup.

DESCRIPTION OF THE PREFERRED EMBODIMENT

A horizontal conveyor 10, moving at a constant speed carries a vertically standing glass container (a bottle) 11 through the illustrated inspection location. At this location a pair of light sources 12 which can be short arc flash tube strobes and which are located behind the conveyor direct diffused back light horizontally, past the bottle at an angle of approximately 45° to the conveyor. As a result, these beams 14 of diffused light intersect perpendicularly through the vertical axis 15 of the bottle when it is located at the inspection location. These beams are larger than the largest container to be inspected so that light will always pass around the entire profile (the sides and top) of a container located at the inspection location. The light from each source is beamed to vertically related mirror pairs 16, 17 (periscopes) which are located in front of the conveyor and which horizontally return the beams to redirecting left back and right back mirrors 18. The redirecting mirrors redirect the beams to the reflecting surfaces 20 of a reflecting prism 22 which aim the beams at a corresponding half of the image of a two-dimensional (CCD) camera 24 (A camera mirror 25 reflects the beams vertically upwardly to the camera which looks vertically downwardly). Both images can be presented on a suitable screen 26 and can be evaluated by an image processing computer 28 which can evaluate both views to make sure that the profile is not defective. This image processing computer will issue an acceptance or rejection signal 30. For example, the neck of the container or the entire container may be bent from its desired location. The outer surface of the bottle may have an annular ripple or settle line or the bottle may be a "freak," i.e., a bottle with an unplanned depression. All of these defects can be identified by the image processing computer 28 that will compare the profile of the container with the ideal profile for that container.

The camera is mounted so that its rotational position can be changed (represented by arrow 30) and it has a zoom lens ring 42 which can effectively independently move the camera towards or away from (represented by arrow 31) the reflecting prism 22 and a focus ring 43 to change the focus (both optionally, may be part of a one touch system). The camera mirror 25 and left and right back mirrors 18 are mounted on three point kinematic mounts. This permits independent movement of these mirrors about horizontal and vertical axes extending in the plane of the mirrors (represented by arrows 32, 34, 36 and 38). The reflecting prism is mounted for translation towards and away from the camera (represented by arrows 40) and the periscopes 16, 17 are mounted on three point kinematic mounts which permit rotation about an axis extending through the lower periscope mirror and bisecting each mirror into horizontally adjacent halves. Rotation about these axes is represented by arrows 42. Rotation about a vertical axis will be referred to as azimuth and rotation about a horizontal axis will be referred to as elevation.

Figure 1:
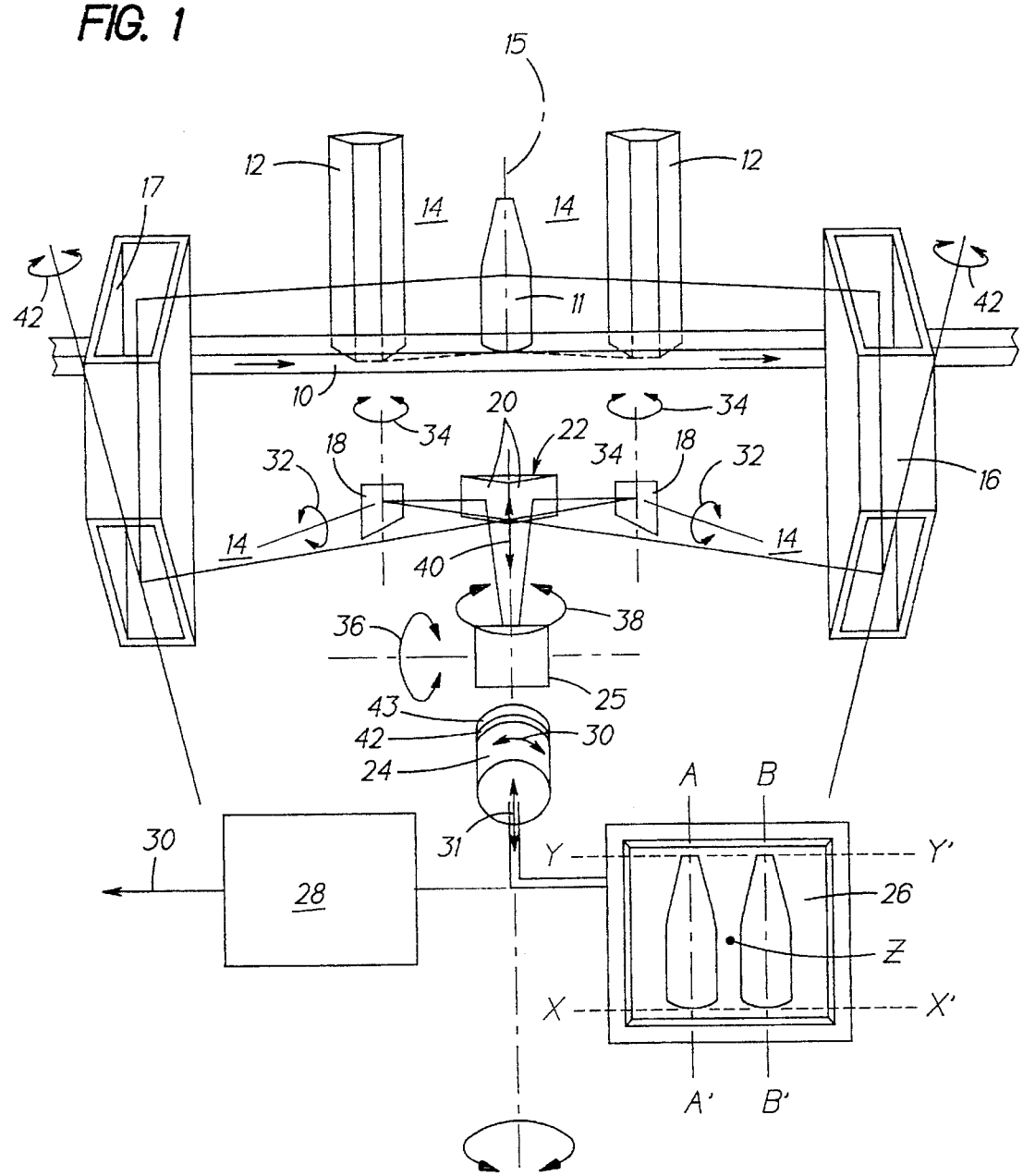
FIG. 1 discloses an oblique schematic view of an inspection machine made in accordance with the teachings of the present invention.

Ideally, if the camera is properly focused, if the axes of the two bottle images coincide with lines A-A' and B-B' (FIG. 1), if the bottle image base rests on line X-X', and if the top of the bottle images engage line Y-Y', then the system is properly aligned. Computer 28 can accordingly evaluate the location and tilt of the axes of the bottle images relative to each other and to lines A-A' and B-B', the location of the bottom and top of each bottle image and their locations relative to ideal, whether the images are rotated about the lens axis Z, the distance out of alignment of each image in terms of side to side displacement, top to bottom displacement and rotation, and whether the images are properly focused.

Figure 3:
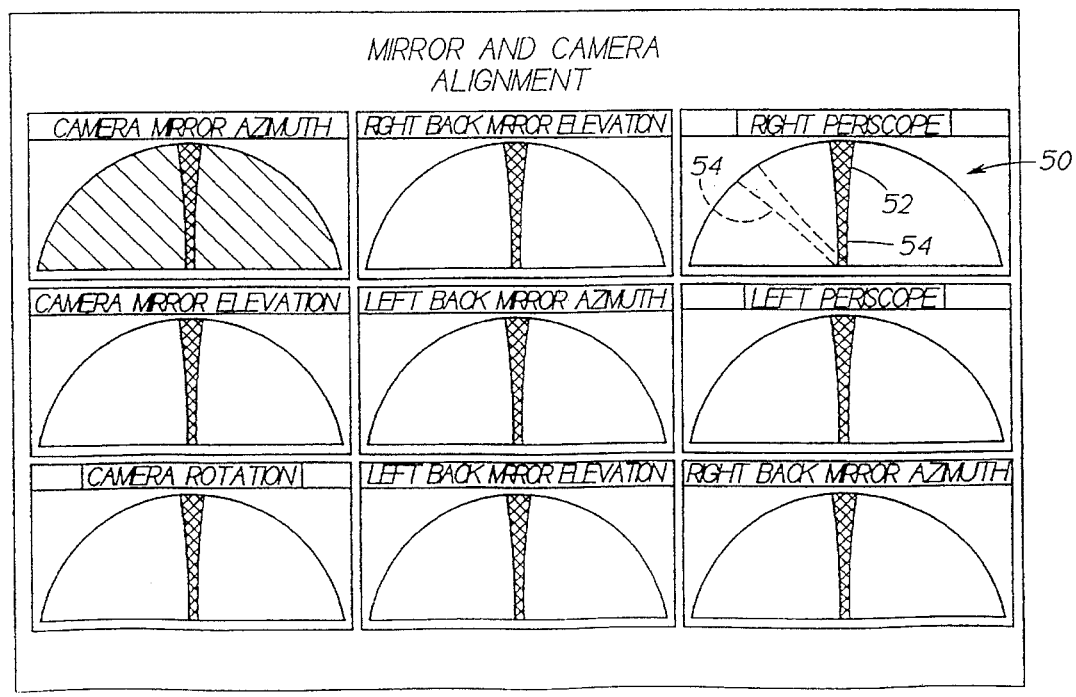
FIG. 3 is a computer screen for the controller of the inspection machine shown in FIG. 1, which presents nine alignment gages used mostly during machine setup.

Each gage 50 (FIG. 3) indicates an acceptable zone 52 and presents a movable indicator or needle 54, which if located in the acceptable zone, will indicate that this element is in proper alignment. These alignment gages will be used during initial machine setup and thereafter mainly during job setup. The gages will be enabled in a selected sequence in some convenient manner as by changing the color of the gage background. The camera mirror azimuth gage is cross hatched to indicate that it has an appearance different from the other gages.

Figure 2:
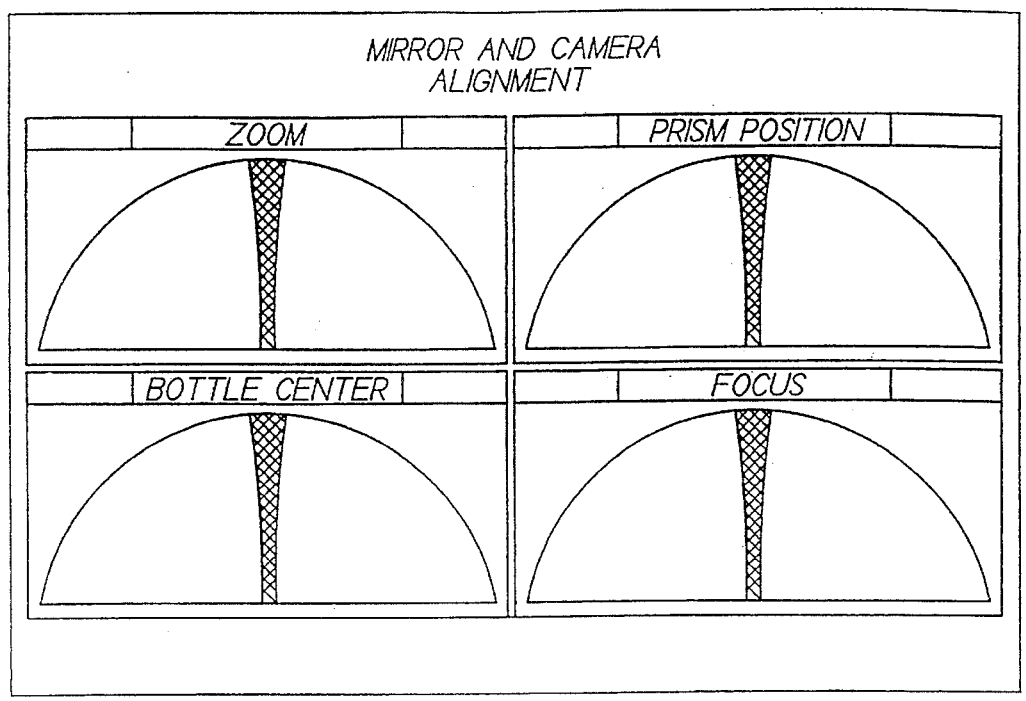
FIG. 2 shows another computer screen presenting four alignment gages: zoom, bottle center, focus and prism position which will be used mostly during job setup.

FIG. 2 shows four gages that will be used after machine setup (for installation and for periodic alignment) for each new job setup.

Zoom—Where the bottle images will not vertically fill (FIG. 4) or are too big for the horizontal band defined by lines X-X' and Y-Y', the indicator in the zoom gage will be located appropriately either to the left or to the right of the acceptable zone. The operator will adjust the zoom lens (which will change the indicator position) until the images properly vertically fill the horizontal band which can be done while looking at the gage. Location of the movable indicator within the acceptable zone will indicate to the operator that the zoom setting is correct. A similar width evaluation will be made which will control for very wide bottles.

Prism Displacement—When the prism reflector is too far (FIG. 5) (or too near) from the camera, the bottle images will either be farther apart than ideal or closer than ideal. The computer indicates this out of alignment in the prism displacement gage so that the operator can correct this prism displacement alignment by displacing the prism via a screw nut mechanism until the indicator moves into the acceptable zone.

The last two gages of the first screen are the bottle center and focus gages. The bottle centered gage is a gage for indicating whether the sensor which starts the inspection process is properly located. A sensing beam (not shown) is interrupted by the leading edge of the bottle and this interruption should occur when the bottle is at the precise inspection location. The sensor can be relocated until the indicator of the bottle centered gage moves into the acceptable zone. The computer can also analyze how rapid the transition is at an image edge and based on this transition rate determine whether the image is properly focused. The indicator in the focus gage will indicate whether the focus is correct (properly aligned or not) and the focus ring can be rotated until the indicator in the focus gage is moved into the acceptable zone.

The nine gages on the second screen (FIG. 3) relate to machine setup.

1. Camera Rotation—The first step is to move (rotate) the left or right back mirror about its vertical axis until a dark bar (the front edge of the reflecting prism and the adjacent space) appears on the sensor of the camera. The computer will determine whether the bar is vertical and to the extent that it is not, which would result in the bottle images appearing to be rotated about the camera lens axis (FIG. 6). The indicator in the camera rotation gage will be located beyond the acceptable zone and the operator will know to rotate the camera to another orientation to bring the indicator into the acceptable zone. The camera is now in alignment with the front edge of the reflecting prism.

2. Camera Mirror Azimuth—When the camera mirror is in azimuth alignment, the right (or left) edge of the bar will appear in the center of the sensor (the images could appear as shown in FIG. 7). The computer will indicate any out of alignment on the camera mirror azimuth gage so that it can be corrected by the Operator by rotating the camera mirror about its vertical axis to move the indicator of the camera mirror azimuth gage into the acceptable zone.

3. Left and Right Periscope Lower Mirror—When either of the periscopes is out of elevational alignment, either the top or the bottom of the bottles will tow in (FIG. 8), i.e., the actual axes of the bottle images will not be parallel. The computer will show this out of alignment on the left and right periscope gages by locating the gage indicators outside of the acceptable zone, so that the operator can correct any out of alignment to locate the indicator of each gage in the acceptable zone.

4. Right and Left Back Mirrors-Elevational—FIG. 9 shows images that are on axes A-A' and B-B' but shows that one image is too high and one image is too low. This indicates that the elevational setting or alignment of these mirrors is off and the indicators of these gages will so indicate. The operator can then make suitable adjustments to these mirrors to bring the indicator in each of these gages into the acceptable zone.

5. Right and Left Back Mirrors-Azimuth—Where the actual image axis of one bottle image is shifted side to side from its correct axis (FIGS. 10 and 11), that back mirror will be out of azimuth alignment. In FIG. 10, the left back mirror azimuth is out of alignment and in FIG. 11, the right back mirror azimuth is out of alignment. The indicator in each of these gages will so indicate so that the operator can make suitable adjustments to these mirrors.

6. Camera Mirror Elevation—When the camera mirror is out of elevational alignment, both images will be the same amount high or low (FIG. 12). The computer will indicate this out of alignment on the camera mirror elevation gage so that the operator can rotate the camera mirror about its horizontal axis to displace the gage indicator into the acceptable zone thereby bringing this mirror into elevational alignment.

FIGS. 14A–C set forth the algorithm which has been above discussed. The algorithm enables or activates, in a step-by-step manner, the gages that are at the time relevant to the alignment process and focuses the operator's activities on one alignment or two parallel alignments at a time. When the last of these gages has been tuned by locating the indicator in its acceptable zone, by carrying out the required adjustment, the system will be properly aligned.

While in the preferred embodiment, all of the gages for job setup or machine setup are presented at one time and highlighted sequentially to inform the operator to take the operator through the alignment process. These gages could instead be presented one at a time (two, where parallel alignments occur, such as with the left and right periscopes gages and the right and left back mirror azimuth or elevation gages). Additionally, the operator may at other times instruct the computer to present any gage on the screen and activate it.

We claim:

1. A machine for-inspecting containers comprising a conveyor for delivering containers one at a time to an inspection location, a CCD camera having a sensor, means for imaging a pair of images of a container at the inspection location on said sensor, said CCD camera and imaging means including a plurality of structures adjustable along or around one axis or independently adjustable about or along two axes to perfect said images on said sensor, computer means including a computer and a screen, said computer including means for evaluating said images on said sensor, means for presenting on said screen a gage for each adjustable structure, each of said gages including means for indicating whether the adjustable structure is in alignment, and means for activating said gages in a selected sequence.

2. A machine for inspecting containers according to claim 1, wherein said CCD camera has a viewing axis and said plurality of adjustable structures comprises a reflecting prism displaceable horizontally along an axis corresponding to the axis of said CCD camera.

3. A machine for inspecting containers according to claim 2, wherein said plurality of adjustable structures comprises a plurality of mirrors selectively rotatable about mutually perpendicular axes.

4. A machine for inspecting containers according to claim 3, wherein said camera is mounted for rotation about the axis of the camera and said plurality of adjustable structures includes said rotatable camera.

5. A machine for inspecting containers according to claim 4, wherein said camera has a zoom lens ring and a focus ring and said plurality of adjustable structures includes said zoom lens ring and said focussing.

6. A machine for inspecting containers according to claim 5, wherein said activating means activates no more than two of said gages at a time.

7. A machine for inspecting containers according to claim 6, wherein said computer comprises means for defining a unique appearance for an activated gage.

8. A machine for inspecting containers comprising a conveyor for delivering containers one at a time to an inspection location, a CCD camera having a sensor, means for imaging a pair of images of a container at the inspection location on said sensor, said CCD camera and imaging means including a plurality of structures adjustable along or around one axis or independently adjustable along or around two axes to perfect said images on said sensor, and computer means for sequentially determining, in a selected order, the extent of any misalignment of said plurality of adjustable structures.

* * * * *